US 9,904,996 B2

(12) United States Patent
Vanbiervliet et al.

(10) Patent No.: US 9,904,996 B2
(45) Date of Patent: Feb. 27, 2018

(54) METHOD OF DETERMINING WEAR ON A DENTAL SCALER TOOL AND TOOL HOLDER THEREFOR

(71) Applicant: DENTSPLY INTERNATIONAL INC., York, PA (US)

(72) Inventors: Joris Vanbiervliet, Kessel-Lo (BE); Jan Heyninck, Mechelen (BE); Kenneth R. Guaragno, Spring Grove, PA (US)

(73) Assignee: Dentsply Sirona Inc., York, PA (US)

( * ) Notice: Subject to any disclaimer, the term of this patent is extended or adjusted under 35 U.S.C. 154(b) by 0 days.

(21) Appl. No.: 15/052,996

(22) Filed: Feb. 25, 2016

(65) Prior Publication Data
US 2016/0247270 A1 Aug. 25, 2016

Related U.S. Application Data

(60) Provisional application No. 62/120,488, filed on Feb. 25, 2015.

(51) Int. Cl.
| | |
|---|---|
| G06K 9/00 | (2006.01) |
| G06T 7/00 | (2017.01) |
| A61C 17/00 | (2006.01) |
| A61G 15/16 | (2006.01) |

(Continued)

(52) U.S. Cl.
CPC ............. *G06T 7/001* (2013.01); *A47G 1/14* (2013.01); *A61C 3/00* (2013.01); *A61C 3/03* (2013.01);

(Continued)

(58) Field of Classification Search
USPC ......... 382/152, 190, 203, 171, 173; 15/22.1; 433/29, 119, 140; 601/142; 310/313.12;
(Continued)

(56) References Cited

U.S. PATENT DOCUMENTS 3,841,891 A * 10/1974 Pallant ...................... G03F 7/00
216/35
5,501,596 A * 3/1996 Bailey ..................... A61C 17/20
433/119

(Continued)

FOREIGN PATENT DOCUMENTS

| EP | 2402740 A1 | 1/2012 |
|---|---|---|
| KR | 1020160016735 A | 2/2016 |
| WO | 9727562 A1 | 7/1997 |

*Primary Examiner* — Anh H Do
(74) *Attorney, Agent, or Firm* — McNees Wallace & Nurick LLC

(57) ABSTRACT

A method in which a digital picture of the tip of a dental scaler tool and other uniquely identifying characteristics is used to measure the extent of wear on the tool. Unique characteristics of the dental scaler tool, such as color and shape of the grip, narrow a set of reference images to a subset of likely matching tip reference images. A digital contour of the worn tip is isolated. Characteristics of the physical shape of each available tips have been stored in a digital library of reference images. The same tip shape characteristics are developed for the tip contour that were stored for each reference image. The digital profile of the worn tip and a matching, selected reference image of the tip from a library of digitally overlaid. An accurate measurement of the extent of wear of the insert tip is made and displayed.

21 Claims, 12 Drawing Sheets

(51) Int. Cl.
*A47G 1/14* (2006.01)
*A61C 3/00* (2006.01)
*A61C 3/03* (2006.01)
*A61C 19/04* (2006.01)
*G06T 7/33* (2017.01)

(52) U.S. Cl.
CPC ............ *A61C 17/005* (2013.01); *A61C 19/04* (2013.01); *A61G 15/16* (2013.01); *G06T 7/337* (2017.01); *G06T 2207/10024* (2013.01); *G06T 2207/20116* (2013.01); *G06T 2207/20228* (2013.01); *G06T 2207/30164* (2013.01)

(58) Field of Classification Search
USPC .............. 435/5; 216/35; 250/483.1; 356/614
See application file for complete search history.

(56) References Cited

U.S. PATENT DOCUMENTS

| | | | |
|---|---|---|---|
| 5,871,392 A | 2/1999 | Meikle et al. | |
| 6,190,167 B1* | 2/2001 | Sharp | A61C 17/20 433/119 |
| 6,284,457 B1* | 9/2001 | Aida | C12Q 1/6881 435/5 |
| 6,369,375 B1 | 4/2002 | Ishiwata | |
| 6,717,683 B1* | 4/2004 | Wakashiro | G01C 11/00 250/483.1 |
| 7,269,873 B2* | 9/2007 | Brewer | A46B 15/0002 15/22.1 |
| 7,448,109 B2* | 11/2008 | Brewer | A46B 15/0002 15/22.1 |
| 7,876,030 B2* | 1/2011 | Taki | A61B 17/320068 310/323.12 |
| 8,371,848 B2* | 2/2013 | Okawa | A61B 1/24 433/29 |
| 8,467,072 B2* | 6/2013 | Cramer | G01B 11/03 356/614 |
| 8,491,300 B2* | 7/2013 | Ziemba | A61C 1/088 433/29 |
| 8,613,616 B2* | 12/2013 | Rose | A61C 1/0015 433/140 |
| 9,064,427 B2* | 6/2015 | Shibui | G09B 23/28 |
| 9,482,755 B2* | 11/2016 | Cramer | G01S 17/66 |

* cited by examiner

METHOD OF DETERMINING WEAR ON A DENTAL SCALER TOOL AND TOOL HOLDER THEREFOR

CROSS-REFERENCE TO RELATED APPLICATIONS

This application claims priority to and the benefit of U.S. Provisional Patent Application No. 62/120,488 filed Feb. 25, 2015, which is hereby incorporated by reference in the entirety.

FIELD OF THE INVENTION

The present invention relates generally to dental instruments used for cleaning a patient's teeth. More particularly, the invention relates to a method for accurately determining wear of a dental scaler tool.

BACKGROUND OF THE INVENTION

Dental professionals, such as dental hygienists, use a variety of dental instruments to clean a patient's teeth. Among the dental instruments used are dental scaler tools. Dental scaler tools driven by magnetostrictive and piezoelectric devices are used to mechanically scale and clean a patient's teeth. With use of the tool over time, the dental scaler tool wears to a degree such that continued use of the dental scaler tool becomes ineffective or uncomfortable and may cause a hygienist to use excessive pressure while scaling which may result in discomfort for the patient and the hygienist.

In the past, dental professionals, such as dentists, would replace worn dental scaler tools based upon their perceived understanding of when the tool became ineffective. A paper template has been available with a silhouette of various tips, each having two spaced line segments extending perpendicularly across the tip near the distal end. The dental scaler tool was placed on or near the paper over a silhouette of the tip type being evaluated for wear. If the distal end of the tip extended past the line segment closer to the distal end of the silhouette, the tip was considered to be appropriate for continued use. If the distal end of the tip did not extend past the line segment more distant from the distal end of the silhouette, the dental scaler tool was considered to be inefficient and should be taken out of service. However, the accuracy of an evaluation of wear of the tip of a dental scaler tool using this method could be impacted by the accuracy of positioning the tip relative to the silhouette, or the effects of parallax due to the angle from which the tip and template are viewed and any distance between the template and the tip, coupled with the small distance being evaluated, could lead to inaccurate evaluation of the extent of wear on the tip of a dental scaler tool. For example, a dental scaler tool that was worn but was still acceptable for continued use may be interpreted as inefficient and be taken out of service prematurely. Conversely, a dental scaler tool that has sufficient wear that warrants being taken out of service may be interpreted as worn but still appropriate for continued use.

The method of the invention provides an improved, robust process that more accurately and more consistently determines the extent of wear on the tip of a dental scaler tool and provides outputs that are easily interpreted while avoiding the shortcomings of previous techniques. The method may employ a holder for holding the dental scaler tool during a step in the process.

BRIEF DESCRIPTION OF THE INVENTION

A method in which a digital picture is taken of the tip of a dental scaler tool and other identifying characteristics that uniquely identify the model of the dental scaler tool. The photograph may be taken while the dental scaler tool is positioned in a holder. Unique characteristics of the dental scaler tool, such as color and shape of the grip, are used to narrow a set of reference images to a subset of likely matching tip reference images. Characteristics of the physical shape of each available tip have been stored in a digital library of reference images. A digital contour of the worn tip is isolated. The same characteristics of the physical shape of the tip contour as were stored for each reference image tip, such as the shape of the tip on the same predetermined coordinate system having an origin at a common reference point, are developed for the worn tip for comparison to reference images to identify a match. The digital profile of the worn tip and a matching, selected reference image of the tip of a new dental scaler tool from a library of digitally stored new tip reference images are overlaid. An accurate measurement of the extent of wear of the insert tip is made and displayed. The extent of wear can be compared to one or more thresholds, such as a first threshold wear level that indicates a fifty percent effectiveness due to wear, and a second threshold that indicates the effectiveness of the tip has been reduced to the extent the dental scaler tool should be replaced. The output can be provided in many different forms, to various devices, including a color code that provides a first color if the wear is in a range of acceptable efficiency, a second color if the wear is in a range of decreased efficiency, and a third color if the efficiency of the tool is such that the tool should be replaced.

Other features and advantages of the present invention will be apparent from the following, more detailed description, taken in conjunction with the accompanying drawings which illustrate, by way of example, the principles of the invention.

BRIEF DESCRIPTION OF THE DRAWINGS

FIG. 8 B is an illustration of a binary image of black or white of the tip.

FIG. 8 C is an illustration of the contour of the tip.

FIG. 9 B is an illustration of a binary image of black or white of the grip.

FIG. 9 C is an illustration of the contour of the grip.

FIG. 11 B is an illustration of another dental tool tip contour retained in digital form in a library of reference tip images.

FIG. 11 C is an illustration of yet another dental tool tip contour retained in digital form in a library of reference tip images.

FIG. 11 D is an illustration of yet another dental tool tip contour retained in digital form in a library of reference tip images.

FIG. 11 E is an illustration of yet another dental tool tip contour retained in digital form in a library of reference tip images.

FIG. 12 B is a portion of FIG. 12 A that illustrates how wear is assessed.

Wherever possible, the same reference numbers will be used throughout the drawings to represent the same parts.

DETAILED DESCRIPTION OF THE INVENTION

Figure 1:
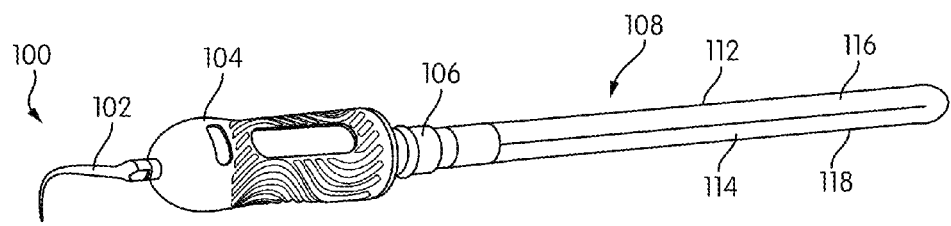
FIG. 1 is a perspective view of an ultrasonic dental scaler insert.

FIG. 1 shows a perspective view of an ultrasonic dental scaler insert 100. An ultrasonic dental scaler insert 100 is a complex tool used by dental professionals to remove plaque from a patient's teeth. Insert 100 includes a metal tip 102, a rubber or rubber-like grip 104, a connecting body 106, and a metal stack 108. The tip 102 may have a water conduit (not shown) for discharging water for cooling purposes and to carry dislodged plaque away from tooth surfaces being cleaned. The connecting body 106 and metal stack 108 are substantially identical in length and cross-section dimensions for many insert 100 designs, so as to fit in and be used with a common hand piece 110 design. The connecting body 106 and metal stack 108 have dimensions that enveloped by a tubular hand piece (not shown). The metal stack 108 has a cross-section shape which is substantially a square having two opposed parallel sides 112, 114 and opposed convex and concave walls 116, 118. Insert 100 can be rotated in the hand piece so the tip can be rotated as needed during use. The metal stack 108 is coupled to a power supply (not shown) by a cord (not shown) extending from the hand piece. A water supply (not shown) may be coupled to the hand piece to provide water to the tip 102 through the hand piece.

Figure 2:
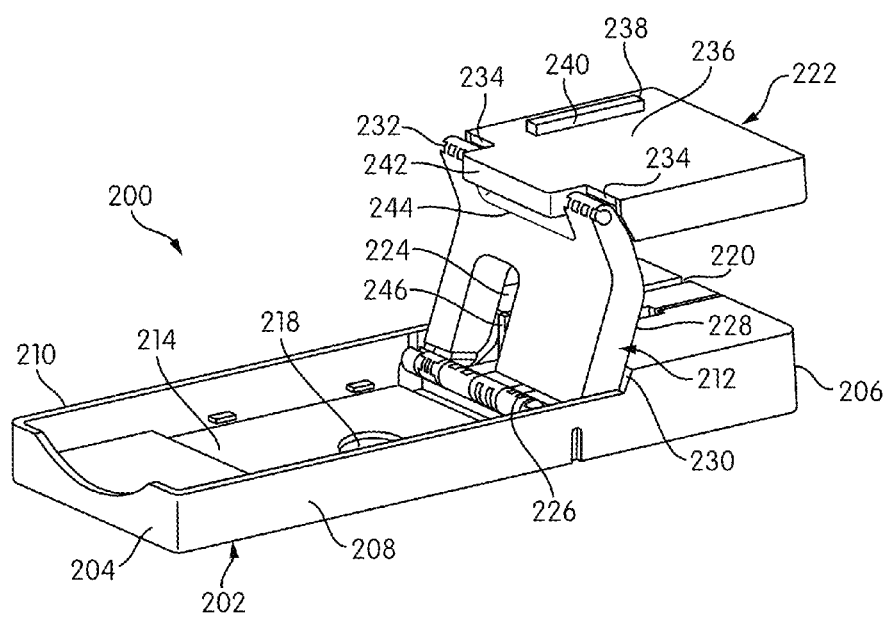
FIG. 2 is an embodiment of a dental scaler insert holder.

FIG. 2 shows an embodiment of a dental scaler insert 100 holder 200. Holder 200 has a base member 202 having front and rear walls 204, 206 and sidewalls 208, 210. Extending upwardly from base member 202 is a vertical support 212. Forward of support 212, within front wall 204 and side walls 208, 210 is a region 214. Some embodiments of the holder 200 have an aperture 218 in the region 214.

Base member 202 includes a recess 220 aligned with aperture 224 in vertical support 212 and extends under platform 222. The recess will be described in greater detail below. The vertical support 212 is coupled to the base member 202 in any known method. In some embodiments, vertical support 212 is rotatably secured to base member 202 by a hinge 226. In FIG. 2 vertical support 212 is rotated (clockwise from the perspective of FIG. 2) into an upright position in which surface 228 of vertical support 212 engages a surface 230 of base member 202.

Platform 222 is secured to vertical support 212 in any known technique. In some embodiments, platform 222 is rotatably secured to vertical support 212 by a hinge 232. In FIG. 2 platform 222 is rotated (clockwise from the perspective of FIG. 2) into a horizontal position in which surface 234 of platform 222 engages a portion of surface 228 of vertical support 212 such that the upper surface 236 of platform 222 is parallel to the bottom 304 of recess 220. Forward edge 242 of platform 222 clears the aperture 244 in vertical support 212 when platform 222 and vertical support 212 rotate (counterclockwise from the perspective of FIG. 2) to be received between sidewalls 208, 210 and front wall 204. Some embodiments of holder 200 may have a ridge 238 on upper surface 236 with a vertical sidewall 240 that is parallel to a center line of recess 220.

Figure 3:
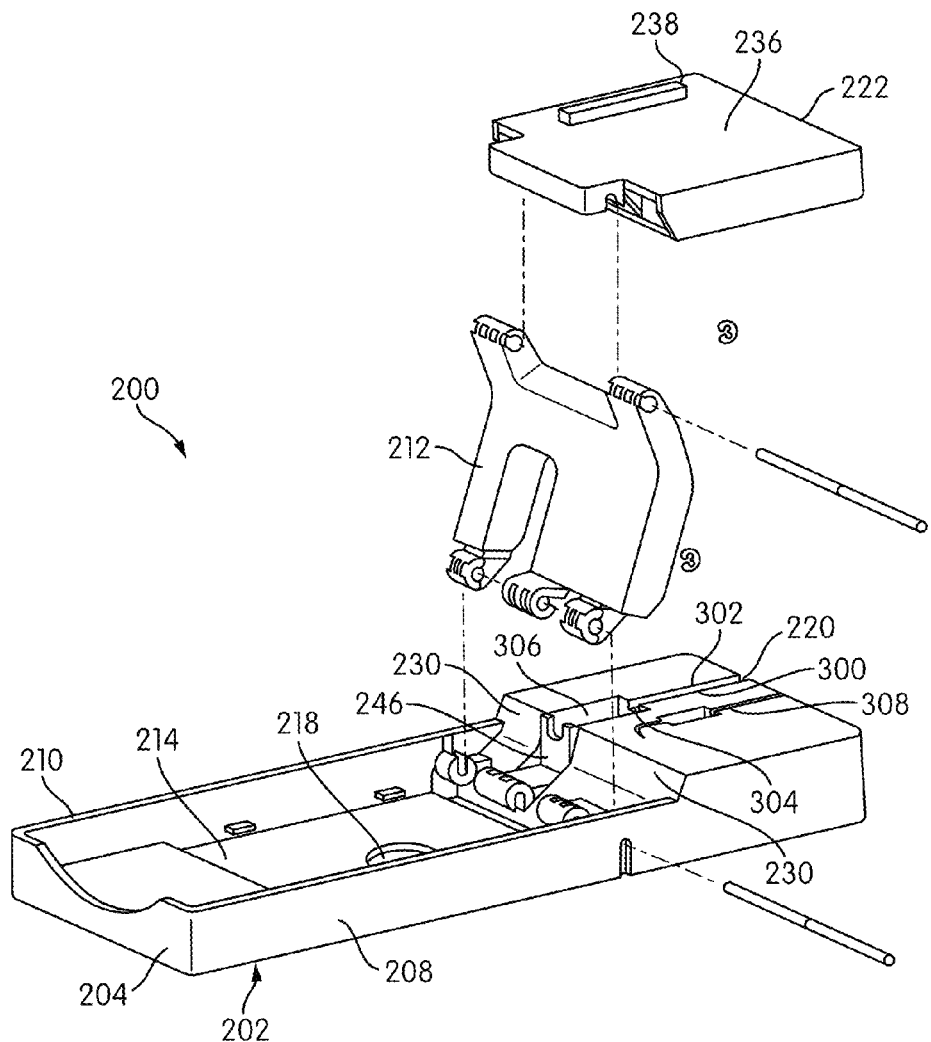
FIG. 3 is an exploded view of the holder of FIG. 2.

FIG. 3 is an exploded view of the holder 200. Recess 220 extends from rear wall 206 toward front wall 204. Recess 220 extends to and opens into a chamber 306 which is sized to receive the connecting body 106. With stack 108 received in recess 220 against bottom 304, the connecting body 106 engages support 246. Side walls 300 and 302 of recess 220 are spaced apart to cooperate with the sides 112, 114 of metal stack 108 when received in and engaging the bottom 304 of recess 220 to prevent roll, pitch, or yaw of the insert 100 in recess 220. The insert 100 has one degree of freedom in recess 220, albeit with limited range of movement. The insert 100 can be moved along the axis of insert 100 toward, or away from, front wall 204. In some embodiments a cross-section of the metal stack 108 is substantially square with sides 112, 114 being parallel, a convex surface 116 and a concave surface 118. Sides 112, 114 of the metal stack 108 cooperate with the sidewalls 300 and 302 of the recess 220 to limit movement of the insert 100. In some embodiments, metal stack 108 is received in recess 220 with concave surface 118 oriented downward.

Although recess 220 has been described as extending from the from rear wall 206 toward front wall 204 opening into chamber 306 and having side walls 300 and 302 that cooperate with the sides 112, 114 of metal stack 108 to prevent roll, pitch, or yaw of the insert 100 in recess 220, the invention is not limited thereto. Engagement between walls of the channel and surfaces of the metal stack 108 need only be sufficient to prevent the insert from rotating so a photograph can be taken. The actual distance of engagement between the channel and the metal stack 108 may be very small, and the engagement may involve convex surface 116 or concave surface 118, or both, instead of or in addition to one or both of sides 112, 114. For example, the metal stack could rest on a thin support having two sidewalls or the support could provide an upper and a lower surface to engage the metal stack to prevent the insert from rotating. In addition, the metal stack could be clamped against a surface to prevent the insert from rotating. While some of the above variations of means for preventing the insert from rotating may retain the connecting body support, not all variations would. Alternatively, another portion of the insert could be secured to prevent the insert from rotating.

Figure 4:
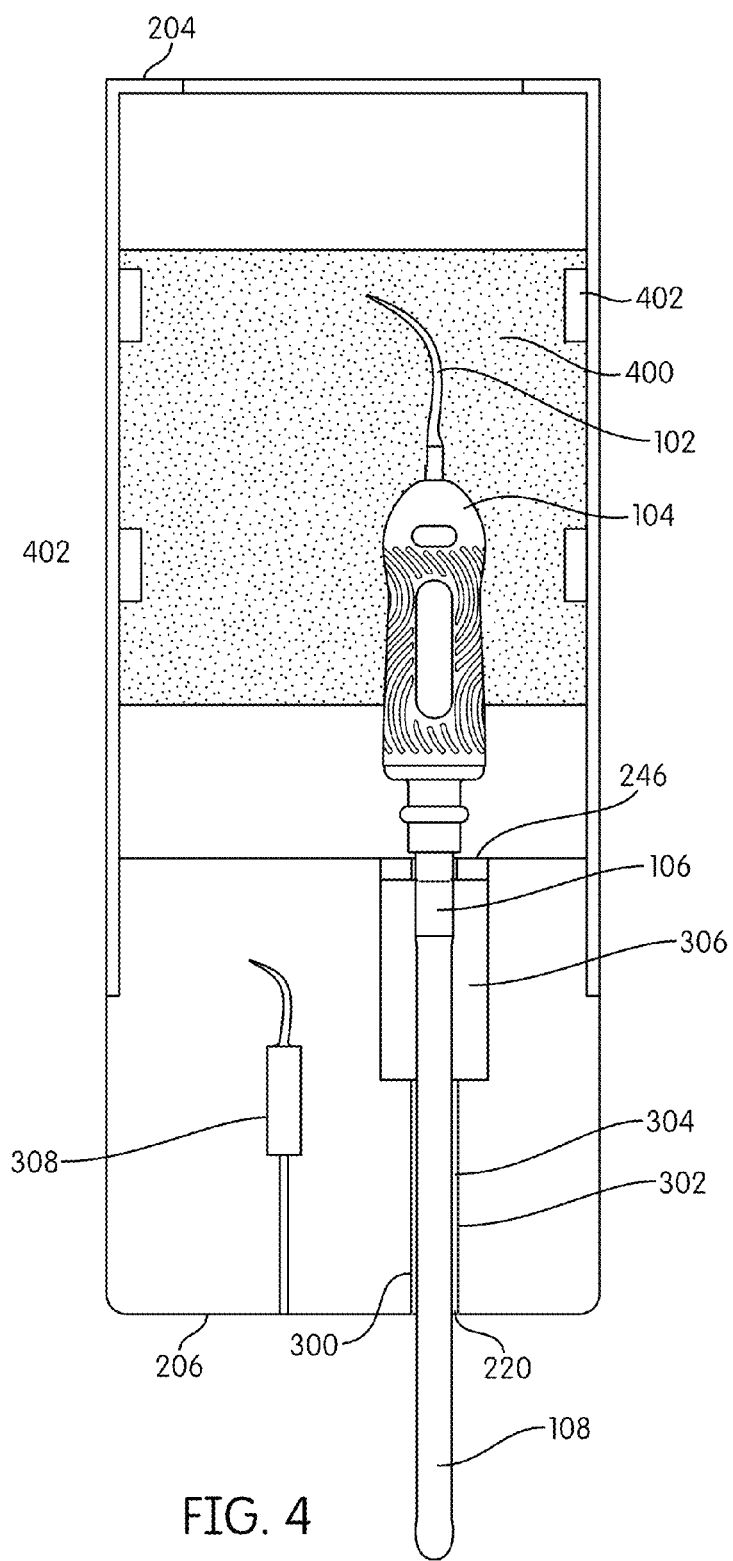
FIG. 4 is a plan view of the base member of the dental scaler tool holder with a dental scaler insert positioned in the holder.

FIG. 4 is a plan view of the base member 202 of the dental tool holder 200 with vertical support 212 and platform 222 removed. An insert 100 is positioned in base member 202 with metal stack 108 received in recess 220, connecting body 106 received in chamber 306 and supported by connecting body support 246. Recess 220 is positioned to a side of a centerline, from front wall 204 to rear wall 206, of base member 202. With recess 220 positioned to the a side of the centerline of base member 202, the tip 102 of insert 100 positioned in recess 220 is oriented to point toward side wall to position the entire tip and the portion of the grip 104 to be photographed over the matte finish material 400.

The entire tip 102 and at least a portion of grip 104 are positioned over region 214 which has the non-reflective, matte finish material 400 positioned therein. The matte finish material 400 eliminates reflected light when a photograph is taken of the tip 102 and grip 104 and also provides a background for the tip 102 and grip 104 that will provide a contrast with the tip 102 and grip 104 in subsequent image processing. An example of a non-reflective, matte finish material 400 is black velvet, however, the invention is not limited thereto. In some embodiments, the matte finish material 400 is retained by tabs 402. Aperture 218 in the region 214 is used to facilitate inserting, positioning and removing the matte finish material 400.

Insert 100 can be moved toward or away from front wall 204 to position more or less, respectively, of grip 104 over the matte finish material 400. A sufficient portion of grip 104 should be positioned over the matte finish material 400 to be able to determine the color of the grip 104 as well as any misalignment of a photograph with the grip 104. Such misalignment or deviation angle, if any, is due to incorrect orienting of the smart phone 600 or the camera generally, and will need to be determined and corrected to assure an accurate measurement of wear of the tip 102. In a preferred embodiment, at least fifty percent of the length of the grip 104 would be in the photograph.

Figure 5:
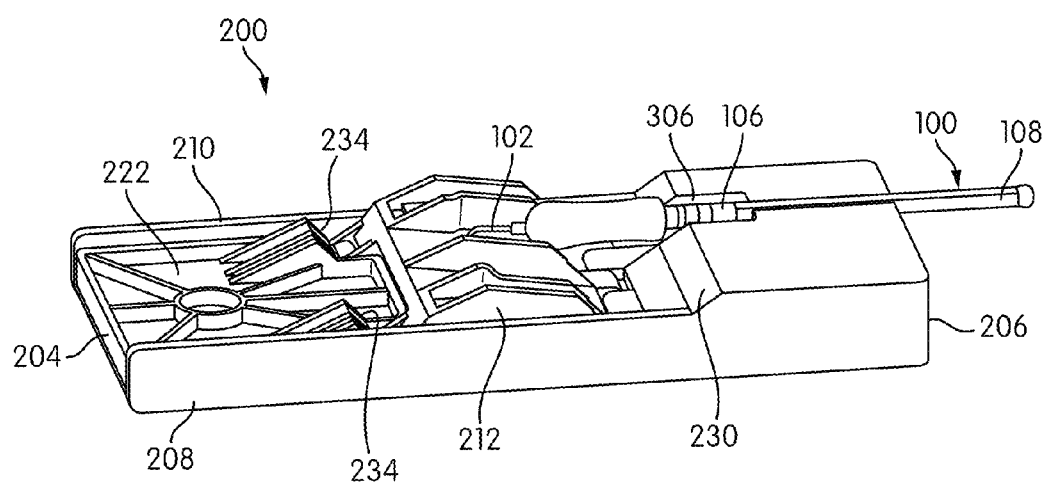
FIG. 5 is a perspective view of the base member of the dental scaler tool holder folded into a low profile position.

FIG. 5 is a perspective view of the dental tool holder 200 folded into a low profile position. Platform 222 and vertical support 212 are rotated counter clockwise from the perspective of FIG. 4 to form a compact, low profile with the platform 222 and vertical support 212 positioned between sidewalls 208, 210, and front wall 204. Insert 100 can be positioned with stack 108 received in recess 220 prior to platform 222 and vertical support 212 being rotated clockwise from the respective low profile positions.

Figure 6:
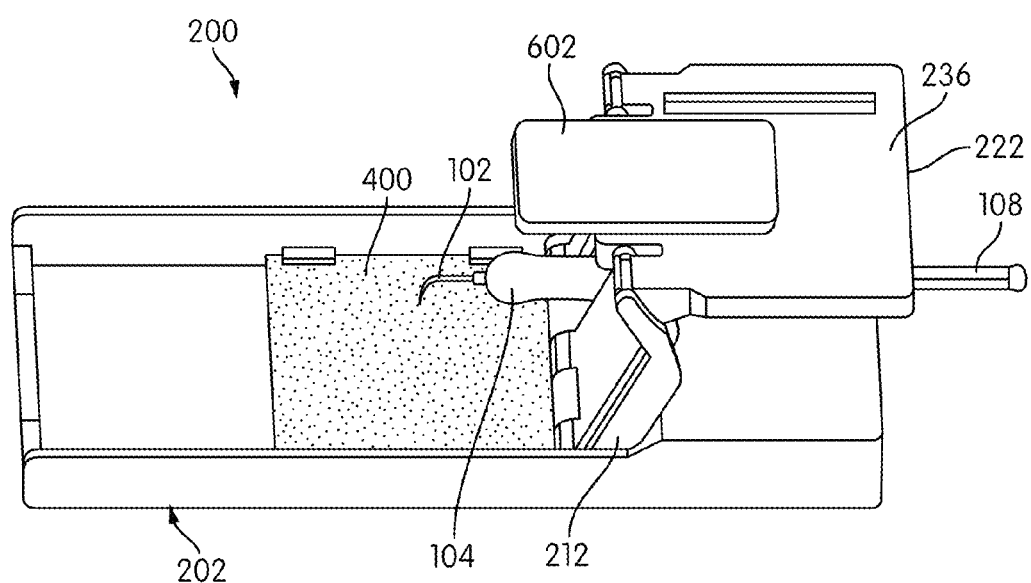
FIG. 6 is a perspective view of the dental scaler tool holder of FIG. 2 with a dental scaler tool and a smart phone positioned on the holder.

FIG. 6 is a perspective view illustrating the dental tool holder 200 with a dental scaler tool and a smart phone 600 positioned on the holder 200. Smart phone 600 is positioned on platform 222 with the camera oriented to take a photograph of tip 102 and grip 104 of insert 100 and may or may not have a side against vertical sidewall 240 of ridge 238. Positioning smart phone 600 on upper surface 236 of platform 222 conterminous with vertical sidewall 240 of ridge 238 aligns the side of a substantially rectangular shaped smartphone 600 to be parallel to the axis of insert 100. If the smart phone 600 on the upper surface 236 of platform 222 touches the vertical sidewall 240 of ridge 238 at one point and is separated from sidewall 240 at all other points, a centerline of the smart phone 600, although in a plane parallel to the centerline of insert 100, will form a small angle of deviation from being parallel to the centerline of insert 100. Angles of deviation both small and large can be compensated for in the software as described in more detail below.

As indicated by the illustration 308, insert 100 should be positioned with the metal stack 108 in recess 220 such that the tip 102 points to the left to position the tip 102 over matte finish material as seen from the perspective of FIG. 6. Metal stack 108 constrained in recess 220 by recess sidewalls 300, 302. Concomitantly, photographs taken using the smart phone 600 positioned with side against ridge 238 will have a center line that is parallel to the centerline of insert 100. A picture of a dental scaler tool taken with a digital camera should be taken with the camera view being perpendicular to the plane formed by the centerline of the tip. Recess 220 cooperating with stack 108 maintains the tip 102 oriented in a plane perpendicular to the view of a smart phone on platform 222.

Figure 7:
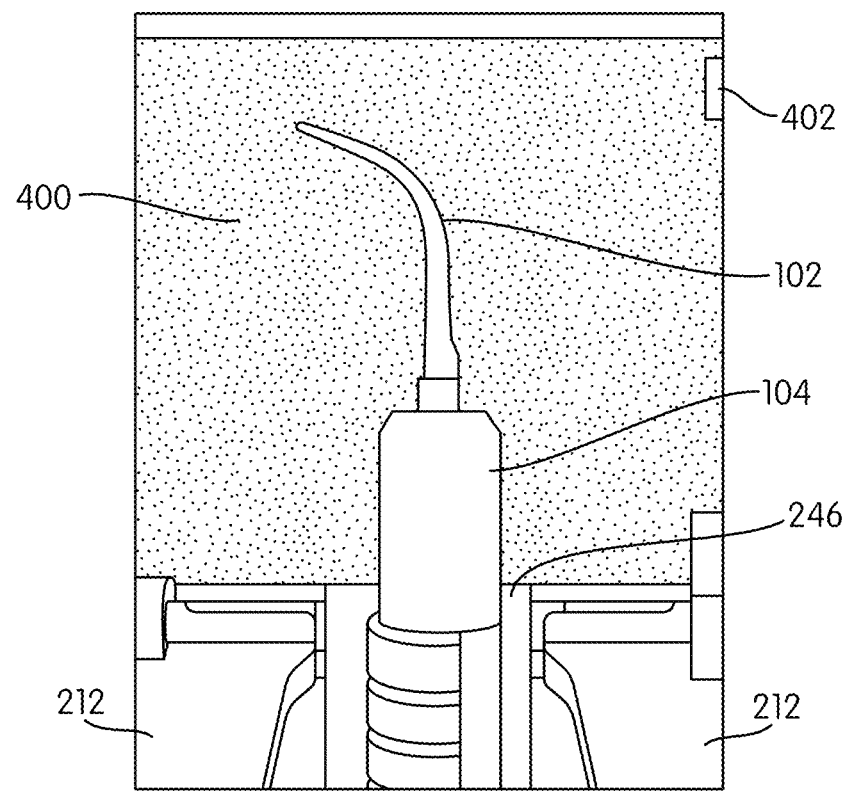
FIG. 7 illustrates a digital photograph of the tip and grip.

FIG. 7 is a digital photograph of the entire tip 102 and part of the grip 104 of insert 100 in holder 200 with matte finish material 400 in the background. The FIG. 7 photograph will be cropped into two photographs for image processing as described below.

Figure 8A:
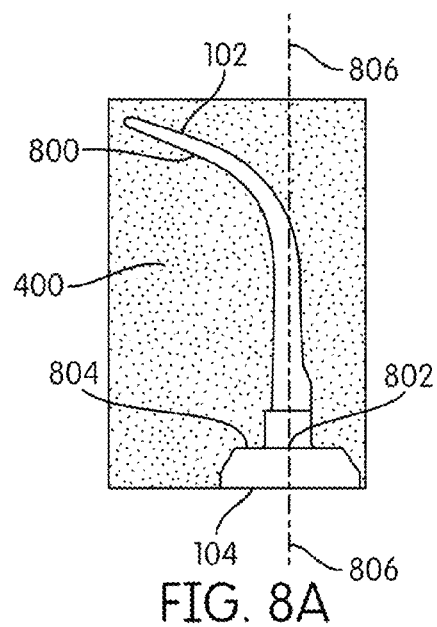
FIG. 8 A is an illustration of the photograph of FIG. 7 cropped, retaining the tip of the dental scaler tool.
Figure 8B:
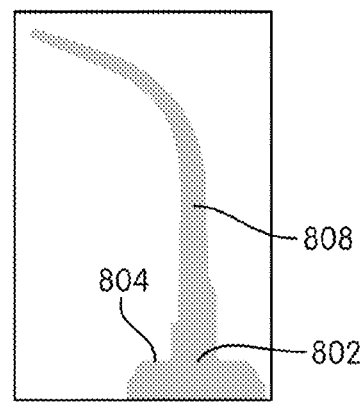

FIG. 8A is a digital image that is a cropped upper portion of the photograph of FIG. 7 retaining all of tip 102 and a small portion of grip 100 with a matte finish material 400 background. Any background that was in the photograph of FIG. 7 that was not matte finish material 400 has been removed by cropping. A distal end 800 of tip 102 is near the upper left corner of the cropped FIG. 8A and the tip 102 is relatively large as illustrated in FIG. 8. A sharp contrast exists between the tip 102 and the matte finish material 400. Similarly, a sharp contrast exists between the grip 104 and the matte finish material 400. A sufficient portion of grip 104 has been retained to identify a tip-grip interface point 802 located at the edge 804 of grip 104 and the intersection of a centerline 806 of a widened region 808 of tip 102. The tip-grip interface point 802 will be a reference point to align an image of tip 102 with a reference image from the digital library of reference images stored in memory. The tip-grip interface point 802 is determined as the point where the (horizontal) width of the tip contour exhibits the largest increase, and in that sense determining the point where the tip ends, and the grip begins.

Figure 8C:
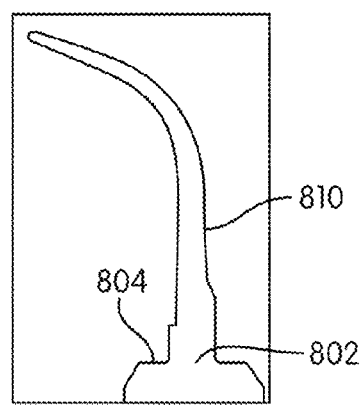

The image illustrated as FIG. 8A is segmented using the NeighborhoodConnectedImageFilter software available from the ITK Organization at the ITk.org website. The ITK software converts the digital image of FIG. 8A, which is considered a gray scale image, into a binary image 810 of black or white as illustrated in the digital image of FIG. 8B. The contour 810 of tip 102, which is also a digital image produced by the ITK.org software, is illustrated in FIG. 8C. The contour 810 is produced as the perimeter of the black-white interface of the digital image in FIG. 8B.

Figure 9A:
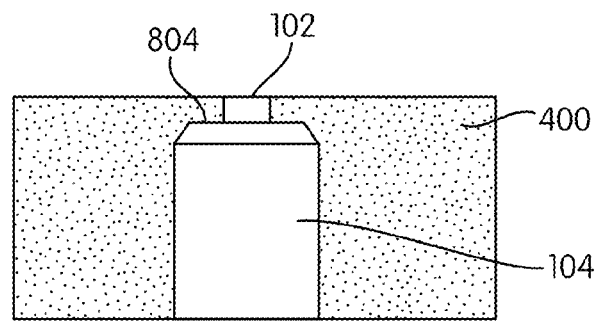
FIG. 9 A is an illustration of the photograph of FIG. 7 cropped, retaining the grip of a dental tool.

FIG. 9A is a digital image that is a cropped lower portion of the photograph of FIG. 7 retaining the grip 104 and a portion of tip 102. Any background that was in the photograph of FIG. 7 that was not matte finish material 400 has been removed by cropping. A sharp contrast exists between the grip 104 and the matte finish material 400. Similarly, a sharp contrast exists between the portion of tip 102 that remains and the matte finish material 400. The image illustrated as FIG. 9A is segmented using the Neighborhood-ConnectedImageFilter software available from the ITK Organization at the ITk.org website. The segmented grip image is used as a mask to select the pixels on the cropped photograph of FIG. 9A that are part of grip 104. The mean color in terms of a hue value of the pixels is then calculated. The hue detection may account for the color of the light source. The final hue value is used to identify the color of the grip 104 as one of blue, green, purple or magenta such as by reference to data presented in FIG. 10. The ITK software converts the digital image of FIG. 9A, which is considered a gray scale image, into a binary image 900 of black or white as illustrated in the digital image of FIG. 9B. The contour 902 of grip 104 and a portion of tip 102, which is also a digital image produced by the ITK.org software, is illustrated in FIG. 9C.

Figure 9B:
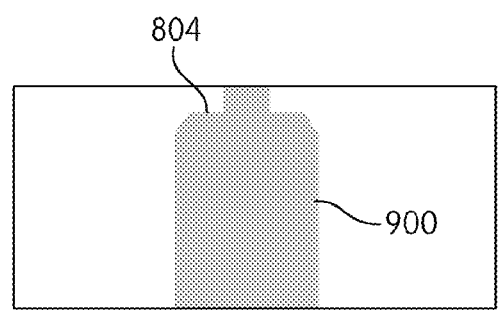
Figure 9C:
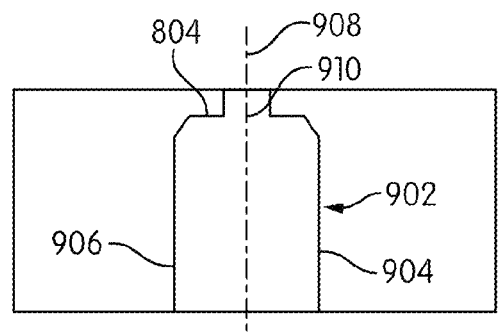

The contour 902 is produced as the perimeter of the black-white interface of the digital image in FIG. 9B. The straight edge portions 904 and 906 of contour 902 are detected and points thereon are used to calculate a set of points half way between the straight edge portions. A straight line is fitted through the points as centerline 908. The centerline 908 intersects edge 804, defining a coincident point 910 that will be overlaid on a corresponding reference point on reference images during a registration step. The centerline 908 is also evaluated for an angle of deviation. The angle of deviation is not due to the insert being misaligned in recess 220. The angle of deviation is due to the smart phone 600 or other digital camera that made the digital photograph of FIG. 7 not being aligned with the centerline of insert 100. The angle of deviation is determined as the angle between the centerline 908 of grip 104 and a vertical edge of the photograph of FIG. 7. The angle of deviation, small or large, may be calculated and compensated for at this stage in the process, or may be calculated and compensated for in the registration step described below. Characteristics of the shape of the grip 104 include geometry of the grip 104, such as but not limited to a bulbous feature, one of a plurality of diameters, and a uniform diameter along the length of the grip 104. Alternate embodiments could, for example, employ a registration of the hand grip shape onto a reference hand grip as it is done herein for registration of the tip.

Figure 10:
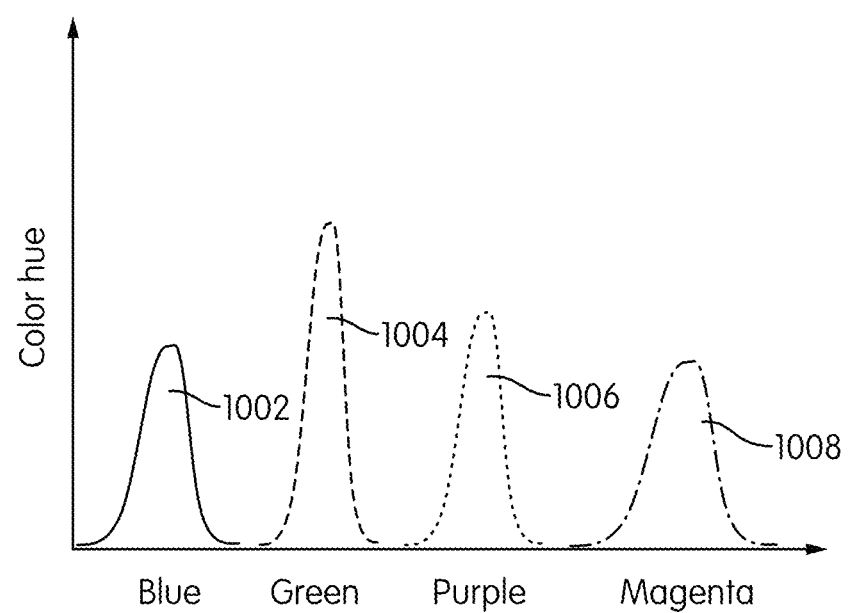
FIG. 10 illustrates the distribution of hue values of four grip colors.
Figure 11A:
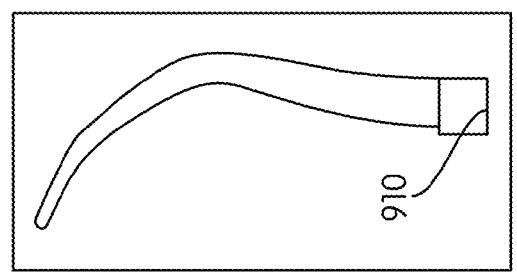
FIG. 11 A is an illustration of a dental tool tip contour retained in digital form in a library of reference tip images.
Figure 11B:
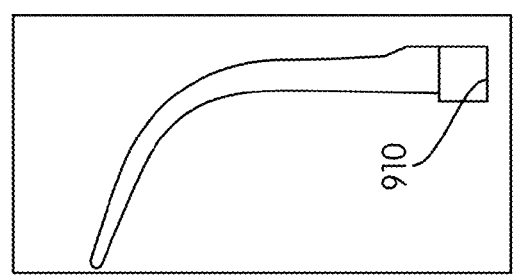
Figure 11C:
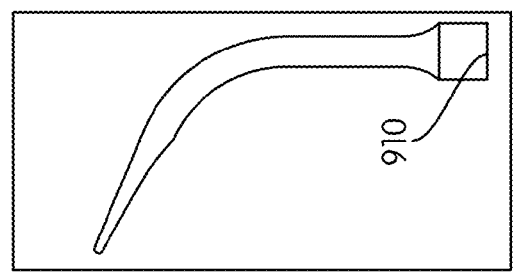
Figure 11D:
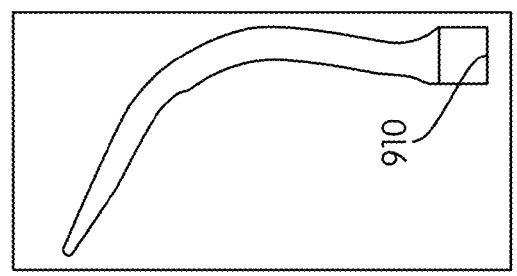
Figure 11E:
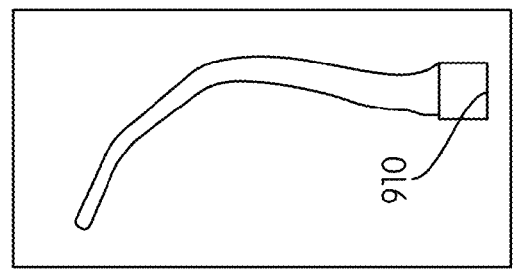

FIG. 10 illustrates the distribution of color values of four colors of grip 104, green, blue, purple and magenta, although the invention is not limited thereto. The color has been converted to a hue value by software from ITK.org, which eliminates variations in saturation and brightness. The curves illustrate the hue values of the respective colors are distinct and can be used as a distinguishing characteristic. Hue values, when taken in combination with other distinguishing characteristics of dental scaler tools, can uniquely identify the model of the insert being evaluated for wear and concomitantly the unique geometry of the tip 102 of an insert 100. The hue value curves were developed from empirical test data. Curve 1002 represents the color blue. Curve 1004 represents the color green. Curve 1006 represents the color purple, and curve 1008 represents the color magenta.

Characteristics of the physical shape of the tip of each reference image have been developed and stored digitally, such as in memory of a smart phone or computer, in a digital library. The physical shape of each tip has been developed on the same coordinate system having an origin at a common reference point, such as the coincident point 910. Each tip shape uniquely identifies a stored reference image tip. The characteristics of the physical shape of a reference image are easily compared to the characteristics of a contour 810 of a worn tip 102.

Unique characteristics of the dental scaler tool, such as color and shape of the grip, narrow a set of reference images to a subset of likely matching tip reference images. A digital contour of the worn tip is isolated. The same characteristics of the physical shape that have been stored for each reference image tip, such as the shape of the tip on the same predetermined coordinate system having an origin at coincident point 910, are developed from the tip contour 810 for the worn tip 102. The characteristics of the physical shape of the worn tip 102 are systematically compared to the corresponding characteristics of the physical shape of reference images from the subset of likely matching tip reference images to identify a match. The matching reference image is selected. A digital profile of the selected reference image and the contour 810 of the worn tip 102 are overlaid one over the other.

The combination of the shape of the tip 100, the shape of the grip 104, and the color of the grip determines which stored reference image is selected to be compared to the tip 102 to evaluate wear. The reference images are stored under a corresponding identifier that is indicative of which combination or combinations of shape of the tip 102, shape of the grip 104, and color of the grip 104 to which each reference image corresponds.

FIGS. 11 A, 11 B, 11 C, 11 D and 11 E illustrate the respective contours of a few of the reference images stored in digital form in memory of the smart phone or a computer system, depending on the system used to measure wear on a dental scaler tool. Each reference image tip is stored as the equivalent of the contour of a new tip with a reference point corresponding to coincident point 910 and an identifier that corresponds to a unique combination of distinguishing characteristics of dental scaler tools. The reference images can be stored with the tip oriented either to the right or to the left as the two views are mirror images of each other. Tips for dental scaler tools have been made in a large variety of shapes to work on and around various tooth and appliances shapes, as well as to work on various materials from which appliances are made. As new tip geometries are developed, or as tip geometries are displaced, the digital library of reference images is easily updated. A reference image can be made of a new, unused tip for each combination of tip shape, grip shape, and grip color, or other defining characteristics. Furthermore, the library of reference images can be expanded as additional identifying characteristics are introduced. The reference images can be made using the process described herein, from engineering drawings, or using any technique suitable for generating references images of sufficient accuracy and clarity as are needed to be used in the disclosed process.

Figure 12A:
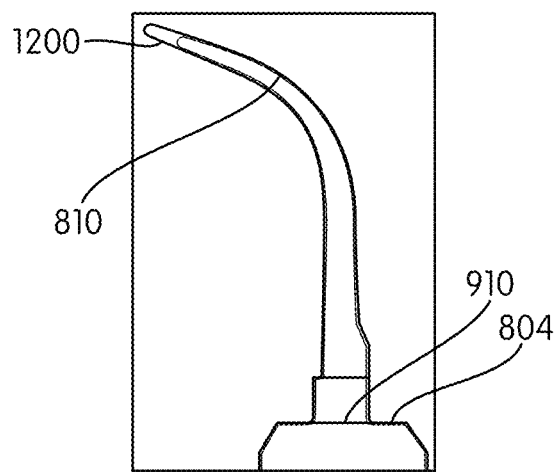
FIG. 12 A is an illustration overlaying the contour of a worn dental tip and a reference tip image.
Figure 12B:
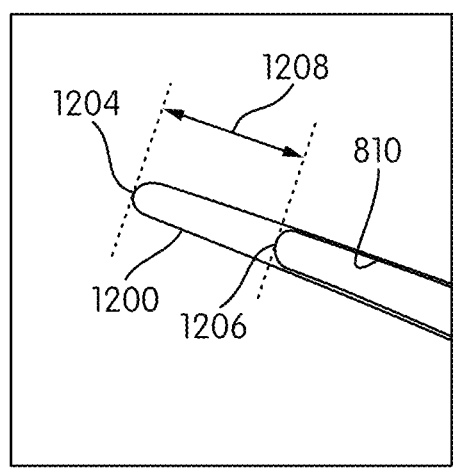

FIGS. 12 A and 12 B illustrate how wear is assessed by overlaying the contour 810 of a worn dental scaler tool tip 102 and a corresponding reference image tip from the library of reference images. In FIG. 12A the reference image tip is illustrated as the outer line 1200. The contour 810 of the dental scaler tool insert 100 tip 102 being evaluated for wear is illustrated as the inner line.

Both the contour 810 and the corresponding reference image tip selected from the library of reference images have a coincident point 910. The contour 810 of a worn dental scaler tool insert 100 tip 102 and the corresponding reference image tip selected from the library of reference images are overlaid, one over the other with the respective coincident points 910 overlying each other. A three step registration is then completed. Registration involves finding a transformation consisting of three elements: a translation, a rotation and a scaling. These three elements could be determined as follows:

For the translation, first the tip coincident point 910 is determined as the point where the (horizontal) width of the tip contour exhibits the largest increase, and in that sense determining the point where the tip ends and the grip begins. The translation is then the displacement vector that translates the coincident point 910 of the tip contour onto the tip base of the reference contour.

Rotation is determined by estimating the angle of deviation of the insert's grip (which was previously extracted from the grip contour) and then rotating the tip contour through an angle of the same magnitude but opposite direction as the angle of deviation. The rotation is around the tip coincident point 910.

The scale is determined by scaling the translated and rotated image (with the values from above) with several values, and choosing the value for which the distance between the tip contour points and the closest reference contour point has the smallest value.

After the extracted outline of the tip 102 and the tip of the selected reference image are overlaid, the wear is calculated as the minimum distance from the reference image tip, endpoint 1204, to the tip 102 of the dental scaler tool being evaluated for wear, endpoint 1206. An accurate measurement of the extent of wear of the insert tip is made and displayed. The extent of wear can be compared to one or more thresholds, such as a first threshold wear level that indicates a fifty percent effectiveness due to wear, and a second threshold that indicates the effectiveness of the tip has been reduced to the extent the dental scaler tool should be replaced. The output can be provided in many different forms, to various devices, including a color code that provides a first color if the wear is in a range of acceptable efficiency, a second color if the wear is in a range of decreased efficiency, and a third color if the efficiency of the tool is such that the tool should be replaced.

The extent of wear may be displayed on a screen. For ease of interpretation, the extent of wear is displayed as one of three colors, green, yellow and red. The color green indicates the wear is less than one millimeter. The dental scaler tool still operates effectively at more than fifty percent efficiency. The color yellow indicates the wear is greater than one millimeter but less than 2 millimeters. The dental scaler tool still operates, but at an efficiency that is less than fifty percent. The color red indicates the wear is greater than 2 millimeters, the dental scaler tool is inefficient and should be taken out of service and replaced.

Figure 13:
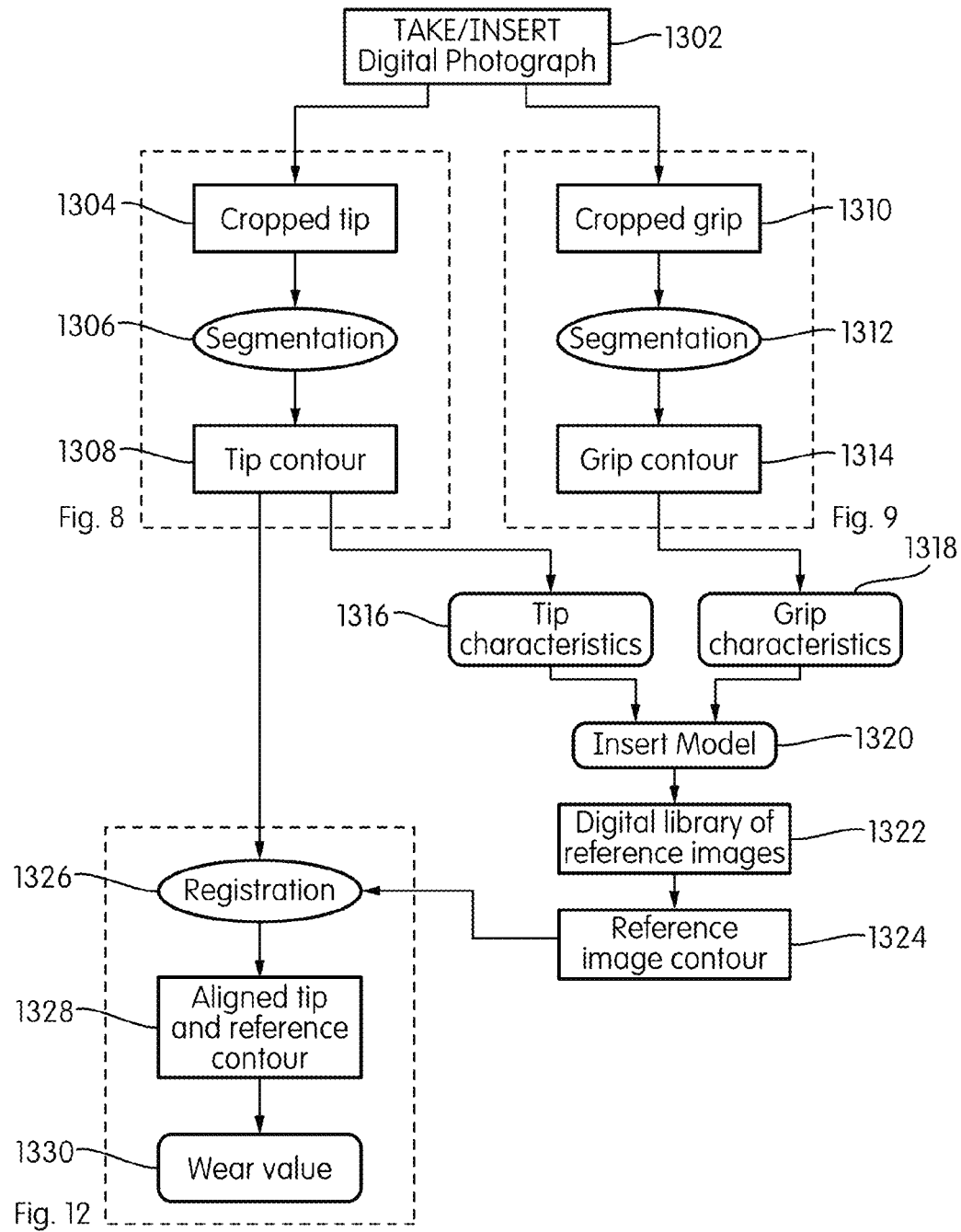
FIG. 13 is a flow diagram illustrating information flow through the process to determine the extent of wear on the tip of a dental scaler tool.

FIG. 13 is a flow diagram illustrating information flow through the process to determine the extent of wear on the tip 102 of a dental scaler tool. The flow diagram applies to both a process using a smart phone or a computer system. A digital photograph is taken of the tip 102 and a grip 104 of a dental scaler tool to determine the extent of wear on the tip, or a photograph of the tip 102 and a grip 104 is transferred into a computer system at 1302. The photograph is cropped to include all of the tip 102 and at least a portion of the grip 104 at step 1304. The cropped photograph is subjected to a segmentation step at 1306. The tip contour 810 is generated at 1308. At 1310, the digital photograph taken or received at 1302 is cropped to include all of the grip 104 and at least a portion of the tip 102 at step 1310. The cropped photograph is subjected to a segmentation step at 1312. The grip contour 902 is generated at 1314. The tip characteristics 1316, including the shape, are provided to contribute to determining the insert model at 1320. The grip characteristics 1318, including geometrical attributes and hue, are provided to contribute to determining the insert model at 1320. The insert model identifier is provided to the digital library at 1322 to access a reference image contour that corresponds to a new, unused, version of the dental scaler tool tip 102 being tested for wear. The reference image contour at 1324 and the tip contour 810 of the dental scaler tool tip at 1308 are subjected to a registration process at 1326. The tip contour 810 and the reference image contour at 1324 are aligned and the wear value is calculated and outputted in an easily understood format.

While embodiments of the invention are described as identifying a particular dental scaler tool by a color of the grip 104, a shape of the grip 104, and a shape of the tip 102, the invention is not limited thereto. These are some of the unique characteristics of the dental scaler tool that can be used to uniquely identify a dental scaler tool model. Other characteristics can be used, alone or in combination with the characteristics employed herein, including a serial number or bar code.

While the invention has been described as using a smart phone for both taking a photograph of the tip and at least a portion of the grip, processing the photograph to determine the shape of the tip, the color hue of the grip, the shape of the grip, and ascertaining whether there is an angle of deviation, the invention is not limited to being carried out on a smart phone. Any digital camera with sufficient resolution can be used to take the digital photographs. The photograph of the tip and at least a portion of the grip could be taken by a digital camera and transferred to a general purpose computer such as by a cable or any other known method including a wireless link, such as but not limited to wireless fidelity, otherwise known as Wi-Fi. Digital cameras that can transfer photographs by Wi-Fi, such as to a computer or other Wi-Fi enabled electronic device, have been publically available for several years. Photographs taken by a digital camera that does not have the capability to transfer photographs by Wi-Fi can be transferred to a smart phone, computer system, or other electronic devices by a cable link.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A method of accurately measuring wear of a dental scaler tool, the method comprising:
   photographing a portion of the dental scaler tool including a tip section and a grip section;
   extracting a contour of the tip section and a portion of the grip section from the photograph;
   determining a shape of the tip section;
   extracting a contour of the grip section and a portion of the tip section from the photograph;
   determining a shape of the grip section;
   determining a color of the grip section;
   based on the shape of the tip section, the shape of the grip section, and the color of the grip section, identifying a model of the dental scaler tool;
   selecting from a library of reference images of dental scaler tool tip profiles, a reference image tip profile of a new dental scaler tool of the same model as the dental scaler tool;
   overlaying one of the extracted contour of the tip section and the selected reference image tip profile over the other, the contour and the reference image each referenced to a common coincident point;
   calculating a distance from a distal end of the contour of the tip section of the dental scaler tool, to a distal end of the reference image tip profile; and
   displaying an extent of wear of the dental scaler tool tip on a smart phone or computer system screen, wherein an output having a first color background is provided when the extent of wear is less than a first threshold representing the tool effectiveness is greater than fifty percent;

wherein an output having a second color background is provided when the extent of wear is greater than the first threshold and less than a second threshold representing the tool effectiveness is less than fifty percent; and wherein an output having a third color background is provided when the extent of wear is greater than the second threshold representing the tool should be taken out of service.

2. The method of claim 1, wherein extracting a contour of the tip section and a portion of the grip section from the photograph further comprises:

segmenting the tip section and a portion of the grip section from the matte finish background.

3. The method of claim 2, wherein extracting a contour of the tip section and a portion of the grip section from the photograph further comprises:

detecting the edge of the tip section and a portion of the grip section as a contour of the tip section and a portion of the grip section.

4. The method of claim 1, wherein extracting a contour of the grip section and a portion of the tip section, further comprises:

segmenting the grip section and a portion of the tip section from the matte finish background.

5. The method of claim 4, wherein extracting a contour of the grip section and a portion of the tip section, further comprises:

detecting the edge of the grip section and a portion of the tip section as a contour of the grip section and a portion of the tip section.

6. The method of claim 1, wherein overlaying one of the extracted contour of the tip section and the selected reference image tip profile over the other, referenced to a centerline of the tip section-grip section interface of the reference image tip profile, further comprises:

registering the extracted contour of the tip section to the reference image by reference to a tip-grip interface point.

7. The method of claim 1, wherein calculating a distance from a distal end of the contour of the tip section of the dental scaler tool, to a distal end of the reference image tip profile, further comprises:

calculating the minimal distance between the distal end of the contour of the tip section of the dental scaler tool and the distal end of the reference tip.

8. The method of claim 1, wherein displaying the extent of wear of the dental scaler tool tip, further comprises:

providing an output having a first color background that is green, a second color background that is yellow, and a third color background that is red.

9. The method of claim 8, wherein a green background represents wear of less than 1 millimeter.

10. The method of claim 8, wherein a yellow background represents wear from 1 millimeter to 2 millimeters.

11. The method of claim 8, wherein a red background represents wear greater than 2 millimeters.

12. The method of claim 8, wherein the output further comprises an illustration of the contour of the tip section and the selected reference image tip profile, one overlaying the other, with a representation of the first and the second thresholds illustrating the extent of wear.

13. A method of using a computer system to accurately measure wear of a dental scaler tool from a photograph of the dental scaler tool that includes a tip section and a grip section, the method comprising:

extracting from the photograph a contour of the tip section and a portion of the grip section;

determining a shape of the tip section;

extracting from the photograph a contour of the grip section and a portion of the tip section;

determining a shape of the grip section;

determining a color of the grip section;

based on the shape of the tip section, the shape of the grip section, and the color of the grip section, identifying a model of the dental scaler tool;

selecting from a library of reference images of dental scaler tool tip profiles, a reference image tip profile of a new dental scaler tool of the same model as the dental scaler tool;

overlaying one of the extracted contour of the tip section and the selected reference image tip profile over the other, referenced to a centerline of the tip section-grip section interface of the reference image tip profile;

calculating a distance from a distal end of the contour of the tip section of the dental scaler tool, to a distal end of the reference image tip profile; and displaying the extent of wear of the dental scaler tool tip.

14. The method of claim 13, further comprising:

photographing a portion of the dental scaler tool including a tip section and a grip section; and transmitting the photograph to the computer system by a wireless link.

15. A non-transitory computer-readable medium comprising one or more computer-readable instructions stored thereon for determining the wear on a dental scaler tool, the one or more instructions, when executed by the computer system, perform the method steps of claim 13.

16. A holder for holding a dental scaler tool while taking a photograph of the dental scaler tool, the dental scaler tool having a tip section, a grip section, a connecting body, and a metal stack, the holder comprising:

a base member having
an area to provide a non-reflective matte finish background for the photograph, wherein the non-reflective matte finish background is removable;

a first support for receiving and supporting the connecting body of the dental scaler tool;

a second support for receiving and supporting the metal stack;

a vertical support extending upwardly above the base member; and a horizontal platform supported by the vertical support, the platform positioned a greater distance from the base member than the first and second supports;

wherein when the dental scaler tool is positioned with the connecting body on the first support and the metal stack on the second support, the tip section and at least a portion of the grip section are positioned over the non-reflective matte finish background; and wherein the platform positioned over the base member such that a smart phone having a camera and laying on the platform is positioned to take a photograph of the tip section and the grip section with the non-reflective matte finish background.

17. The holder of claim 16 wherein the vertical support is rotatably coupled to the base member.

18. The holder of claim 17 wherein the horizontal platform is rotatably coupled to the vertical support.

19. The holder of claim 16 wherein the non-reflective matte finish background is black velvet.

20. The holder of claim 16, further comprising:
   a ridge on an upper surface of the platform, the ridge having a vertical sidewall positioned to cooperate with a smart phone conterminous therewith to align a photograph taken using the smart phone with a centerline of the metal stack.

21. A holder for holding a dental scaler tool while taking a photograph of the dental scaler tool, the dental scaler tool having a tip section, a grip section, a connecting body, and a metal stack, the holder comprising:
   a base member having
      an area to provide a non-reflective matte finish background for the photograph;
      a first support for receiving and supporting the connecting body of the dental scaler tool;
      a second support for receiving and supporting the metal stack;
   wherein when the dental scaler tool is positioned with the connecting body on the first support and the metal stack on the second support, the tip section and at least a portion of the grip section are positioned over the non-reflective matte finish background; and
   wherein the second support is a channel in the base member, the channel having side walls and a bottom, the side walls of the channel capable of cooperating with a metal stack received in the channel to prevent the dental scaler tool from rotating around the axis of the stack.

* * * * *